US 6,603,542 B1

(12) United States Patent
Chase et al.

(10) Patent No.: US 6,603,542 B1
(45) Date of Patent: Aug. 5, 2003

(54) HIGH SENSITIVITY OPTICAL INSPECTION SYSTEM AND METHOD FOR DETECTING FLAWS ON A DIFFRACTIVE SURFACE

(75) Inventors: Eric Chase, Boxford, MA (US); Jay Ormsby, Salem, NH (US); Abdu Boudour, Newton, MA (US); Sergey Broude, Newton, MA (US); Lloyd Quackenbos, Newburyport, MA (US)

(73) Assignee: QC Optics, Inc., Wilmington, MA (US)

( * ) Notice: Subject to any disclaimer, the term of this patent is extended or adjusted under 35 U.S.C. 154(b) by 0 days.

(21) Appl. No.: 09/688,056

(22) Filed: Oct. 13, 2000

Related U.S. Application Data

(60) Provisional application No. 60/211,643, filed on Jun. 14, 2000.

(51) Int. Cl.[7] .............................................. G01N 21/00
(52) U.S. Cl. .................................................... 356/237.4
(58) Field of Search .......................... 356/237.4, 237.1, 356/237.2, 237.3, 237.5

(56) References Cited

U.S. PATENT DOCUMENTS

| | | | |
|---|---|---|---|
| 4,518,257 A | 5/1985 | Donaldson | |
| 4,532,723 A | 8/1985 | Kellie et al. | |
| 4,794,647 A | 12/1988 | Forgues et al. | |
| 5,085,517 A | 2/1992 | Chadwick et al. | |
| 5,127,726 A | 7/1992 | Moran | |
| 5,155,372 A | 10/1992 | Bowen et al. | |
| 5,200,799 A | 4/1993 | Maruyama et al. | |
| 5,432,607 A | 7/1995 | Taubenblatt | |
| 5,506,793 A | 4/1996 | Straayer et al. | |
| 5,572,598 A | 11/1996 | Wihl et al. | |
| 5,608,453 A | 3/1997 | Gerber et al. | |
| 5,625,193 A | 4/1997 | Broude et al. ............ 250/372 |
| 5,644,393 A | 7/1997 | Nakamura et al. ......... 356/237 |
| 5,737,072 A | 4/1998 | Emery et al. | |
| 5,774,222 A | 6/1998 | Maeda et al. ............... 356/394 |
| 5,903,342 A | 5/1999 | Yatsugake et al. | |
| 6,046,801 A | 4/2000 | Liu et al. | |
| 6,052,478 A | 4/2000 | Wihl et al. | |
| 6,072,897 A | 6/2000 | Greenberg et al. | |
| 6,084,716 A | 7/2000 | Sanada et al. | |
| 6,104,481 A | * 8/2000 | Sekine et al. ............ 356/237.5 |
| 6,122,046 A | 9/2000 | Almogy | |

FOREIGN PATENT DOCUMENTS

EP    1 065 499 A2    1/2001

OTHER PUBLICATIONS

PCT International Search Report dated Nov. 2, 2002.

* cited by examiner

Primary Examiner—Michael P. Stafira
(74) Attorney, Agent, or Firm—Mintz, Levin, Cohn, Ferris, Glovsky & Popeo, PC

(57) ABSTRACT

An improved high sensitivity optical inspection system for detecting flaws on a diffractive surface containing surface patterns includes: a first and a second illumination means for illuminating predetermined regions on the diffractive surface to generate a scattered intensity distribution in response to either a flaw or a surface pattern; means for detecting the intensity level of the scattered intensity distribution at a plurality of locations about the diffractive surface; means for establishing a minimum detected intensity level; means, responsive to the minimum detected intensity level, for indicating the absence of a flaw on the illuminated region of the diffractive surface when the minimum detected intensity level is below a threshold intensity level and for indicating the presence of a flaw on the illuminated region of the diffractive surface when the minimum detected intensity level exceeds the threshold intensity level; and means for moving the diffractive surface to generate a scan pattern on the diffractive surface to inspect the entire surface.

54 Claims, 6 Drawing Sheets

HIGH SENSITIVITY OPTICAL INSPECTION SYSTEM AND METHOD FOR DETECTING FLAWS ON A DIFFRACTIVE SURFACE

RELATED APPLICATION

This application claims priority from Provisional Application Serial No. 60/211,643 filed Jun. 14, 2000, which is herein incorporated by reference.

FIELD OF THE INVENTION

The present invention relates generally to an improved high sensitivity optical inspection system and method for detecting flaws on a diffractive surface with pattern features, and more particularly to a system and method which differentiates between light scattered by a pattern on the surface and light scattered by a flaw.

BACKGROUND

Detection of flaws such as particles, holes, bumps, pits or fingerprints on a surface having diffractive features, such as on a photolithographic mask which is conventionally used in modern semi-conductor photolithography, or any other defect on a patterned surface hereinafter generically referred to as a "plate", is critical to maintaining a high level of quality control.

A system which accomplishes this function is disclosed in U.S. Pat. No. 5,625,193 which is assigned to the same assignee as the instant application and is incorporated herein by reference in its entirety. The system disclosed in U.S. Pat. No. 5,625,193 includes a laser which provides a beam of ultraviolet laser light that is scanned across the entire surface of the plate. The angular intensity distribution sensed by an array of detectors in response to the illumination at each point on the plate surface is used to determine the location and size of flaws on the plate surface.

A need exists for a high sensitivity optical inspection system which differentiates between light scattered by a pattern on the surface of the plate, light scattered by a flaw on the surface the plate and system noise, which overcomes limitations and deficiencies of the prior art.

SUMMARY OF THE INVENTION

It is an object of the present invention to provide an improved high sensitivity optical inspection system for detecting and distinguishing between light scattered from flaws and light scattered from surface patterns defined on a diffractive surface.

Accordingly, the present invention sets forth an improved high sensitivity optical inspection system for detecting flaws on a diffractive surface containing surface patterns. The system includes at least one optical source that provides a first beam. The first beam illuminates a first region of the diffractive surface and generates a first scattered intensity distribution. The optical source further provides a second beam, which illuminates a second region of the diffractive surface and generates a second scattered intensity distribution. A plurality of detectors can be positioned about the diffractive surface to detect the first and second scattered intensity distributions. The detectors are coupled to a detection circuit. The detectors provide the detection circuit with information related to the detected first and second scattered intensity distributions. The detection circuit processes the information related to the detected first and second scattered intensity distributions to determines if a flaw is present on the diffractive surface.

The system further includes a movable mounting table that is adapted to securely retain an object holder. The object holder carries an object, the diffractive surface of which is to be inspected. The mounting table, which has the object holder and object under inspection, can be moved with respect to the first and second beams to generate a scan pattern on the diffractive surface.

The optical source includes a first mirror that receives and redirects an optical beam. The optical beam can be provided by an optical light emitter. The optical beam can be redirected by the first mirror to provide the first beam, which illuminates the first region of the diffractive surface. Similarly, the optical source can further include a second mirror that receives and redirects the optical beam provided by the optical light emitter to provide the second beam. The second beam can illuminate the second region of the diffractive surface. The first and second mirrors can each include an off-axis parabolic mirror. The optical source can also include a pivotable mirror that is oriented to receive the optical beam provided by the optical light emitter.

The pivotable mirror can be pivoted to a first position to redirect the optical beam to the first mirror and the pivotable mirror can be pivoted to a second position to redirect the optical beam to the second mirror.

The optical light emitter can include an ultra violet laser. The ultra-violet laser can project an elliptical beam spot on the diffractive surface. Additionally, the ultraviolet laser beam can be controlled to impinge on the diffractive surface at an angle of approximately 60° from normal to the surface. The beam width can be at least as large as the beam trace pitch to ensure inspection of the regions between revolutions of the sample. The beam trace pitch can be no greater than approximately 3 micrometers.

The plurality of detectors can include a first detector which can be positioned at a first location proximate the diffractive surface to detect the intensity level of the scattered intensity distribution at the first location. A second detector can be positioned at a second location proximate the diffractive surface to detect the intensity level of the scattered intensity distribution at the second location. A third detector can be positioned at a third location proximate the diffractive surface to detect the intensity level of the scattered intensity distribution at the third location. In addition, the first, second and third detectors can be positioned about the diffractive surface at locations where the intensity level of the first and second scattered intensity distributions from the surface pattern is expected to be below a threshold intensity level.

The first beam can be controlled to illuminate the first region defined on the diffractive surface which includes a first group of angular sectors ranging from approximately 342.5°–22.5°, 67.5°–112.5°, 157.5°–202.5° and 247.5°–292.5°. The second beam can be controlled to illuminate the second region defined on the diffractive surface which includes a second group of angular sectors ranging from approximately 22.5°–67.5°, 112.5°–157.5°, 202.5°–247.5° and 292.5°–342.5°.

The detection circuit includes an analog signal processing circuit which is coupled to the detectors. The analog signal processing circuit is further coupled to a digital signal processing circuit. The digital signal processing circuit is further coupled to a computer control and data storage unit. The analog signal processing circuit receives information related to the first and second scattered intensity distributions from the detectors and provides the information to the digital signal processing circuit. The digital signal processing circuit determines a minimum detected intensity level associated with the first and second scattered intensity distributions detected by the detectors. The digital signal processing circuit can process the minimum detected intensity level to determine if a flaw is present on the diffractive surface as well as to determine flaw size.

An encoder defined on the mounting table provides information related to the position of the illuminated region on the diffractive surface. This information can be provided to the detection circuit to enable the detection circuit to further determine the relative location of a detected flaw on the diffractive surface. The location and other information related to the flaws detected on the diffractive surface can be further processed and/or stored in the computer control and data storage unit defined on the detection circuit.

The optical inspection system can further include a display that displays the flaws and their locations.

The mounting table can include a rotatably mounted plate holder and a slideable translation stage. The mounting table can rotate and translate the object holder, which carries the object that includes the diffractive surface under inspection, to establish the scan pattern defined on the diffractive surface. The scan pattern can include a spiral trace that has a plurality of revolutions of the first and second beams on the diffractive surface. The plate holder can be coupled to a rotation control circuit that controls rotation of the plate holder. The translation stage can be coupled to a translation control circuit that controls the linear motion of the translation stage.

The method of using the optical inspection system to inspect a diffractive surface containing surface patterns to detect flaws on the diffractive surface can include illuminating a first region of the diffractive surface with a first beam to generate a first scattered intensity distribution; illuminating a second region of the diffractive surface with a second beam to generate a second scattered intensity distribution; detecting an intensity level of the first and second scattered intensity distributions generated by the first and second beams, the intensity level being detected at a plurality of locations about the diffractive surface; establishing a minimum detected intensity level; processing the minimum detected intensity level to determine if a flaw is present; and moving the diffractive surface to generate a scan pattern on the diffractive surface, the scan pattern covering the entire diffractive surface.

Processing the minimum detected intensity level further includes indicating the absence of a flaw on the illuminated region of the diffractive surface when the minimum detected intensity level is below a predetermined threshold level and indicating the presence of a flaw on the illuminated region of the diffractive surface when the minimum detected intensity level exceeds the predetermined threshold intensity level.

Illuminating the first region of the diffractive surface with the first beam includes illuminating a first group of predetermined angular sectors defined on the diffractive surface. Illuminating the second region of the diffractive surface with the second beam includes illuminating a second group of predetermined angular sectors defined on the diffractive surface.

Illuminating the first group of predetermined angular sectors defined on the diffractive surface with the first beam can include projecting an elliptical beam spot onto the diffractive surface. In addition, illuminating the first group of predetermined angular sectors defined on the diffractive surface with the first beam can include directing an ultraviolet laser beam to the diffractive surface at an angle of approximately 60° from normal to the diffractive surface.

Similarly, illuminating the second group of predetermined angular sectors defined on the diffractive surface with the second beam can include projecting an elliptical beam spot onto the diffractive surface. In addition, illuminating the second group of predetermined angular sectors defined on the diffractive surface with the second beam can include directing an ultraviolet laser beam to the diffractive surface at an angle of approximately 60° from normal to the diffractive surface.

Detecting the intensity level of the first and second scattered intensity distributions generated by the first and second beams includes detecting the intensity level of the first and second scattered intensity distribution at a first location proximate the diffractive surface; detecting the intensity level of the first and second scattered intensity distribution at a second location proximate the diffractive surface; and detecting the intensity level of the first and second scattered intensity distribution at a third location proximate the diffractive surface.

Detecting the intensity level of the first and second scattered intensity distributions further includes detecting the intensity level of the first and second scattered intensity distributions at locations about the diffractive surface where the intensity level of the first and second scattered intensity distributions are expected to be below the threshold intensity level.

Moving the diffractive surface to generate the scan pattern on the diffractive surface can further include rotating and translating the object holder and object, which includes the diffractive surface, to establish a spiral trace with a plurality of revolutions of the first and second beams on the diffractive surface. Rotating and translating the object holder and object having the diffractive surface includes overlapping each said revolution of said spiral trace with adjacent revolutions to insure full inspection of the diffractive surface.

Rotating and translating the object holder and object having the diffractive surface can further include spacing said revolutions no greater than approximately 3 micrometers apart.

Moving the object holder and object having the diffractive surface to generate the scan pattern can further include determining the position of the illuminated region on the diffractive surface. Based on the determined position of the illuminated region on the diffractive surface, the location of flaws on the diffractive surface can be determined. The locations and sizes of the flaws detected can thereafter be stored and/or displayed on a display.

The method of using the optical inspection system can further include determining flaw size.

BRIEF DESCRIPTION OF THE DRAWINGS

The foregoing and other objects of this invention, the various features thereof, as well as the invention itself, can be more fully understood from the following description when read together with the accompanying drawings in which.

DESCRIPTION OF THE PREFERRED EMBODIMENTS

The present invention provides an improved high sensitivity optical inspection system and method for detecting flaws on a diffractive surface. The system and method differentiates between light scattered by a pattern on the surface and light scattered by a flaw.

In the system described in U.S. Pat. No. 5,625,193 the radial orientation of the plate, can result in decreased sensitivity by the detectors to light scattered or diffracted from a flaw or pattern defined on the surface of the plate. With the decreasing size of elements in semiconductor devices, for example, it has become increasingly more important to detect smaller flaws on plates under inspection. When the orientation of a first edge of the plate is nonorthogonal to the laser light beam (for example, 45°), which is used to probe the surface under inspection, a diffracted light beam can be substantially detected with maximum intensity by a first detector included in the system. As the plate is slowly rotated to scan the laser beam over the surface under inspection, the diffracted light beam detected by the first detector is reduced and the diffracted light beam detected by a second detector is increased.

As the plate continues to rotate to a position diagonal to a second edge of the plate, the maximum intensity of the diffracted light beam will be substantially detected by the second detector. Therefore, after each 90° of revolution of the plate, the maximum intensity of the diffracted light beam will be substantially detected by either the first detector or the second detector. However, when the edge of the plate is orthogonal to the incident laser beam, both the first and second detectors can detect the reduced intensity diffracted light beam from the surface under inspection.

The reduced intensities of the diffracted light detected by both the first and the second detectors contribute to the overall decrease of the system's sensitivity to pattern scattering. As a result, actual flaws on the surface under test can be accurately distinguished from diffracted light from a pattern on the surface under test or noise from the system.

Therefore, the reduced intensity diffracted light beam detected by both the first and second detectors can result in a higher sensitivity of the system to minute flaws present on the surface under inspection.

Figure 1:
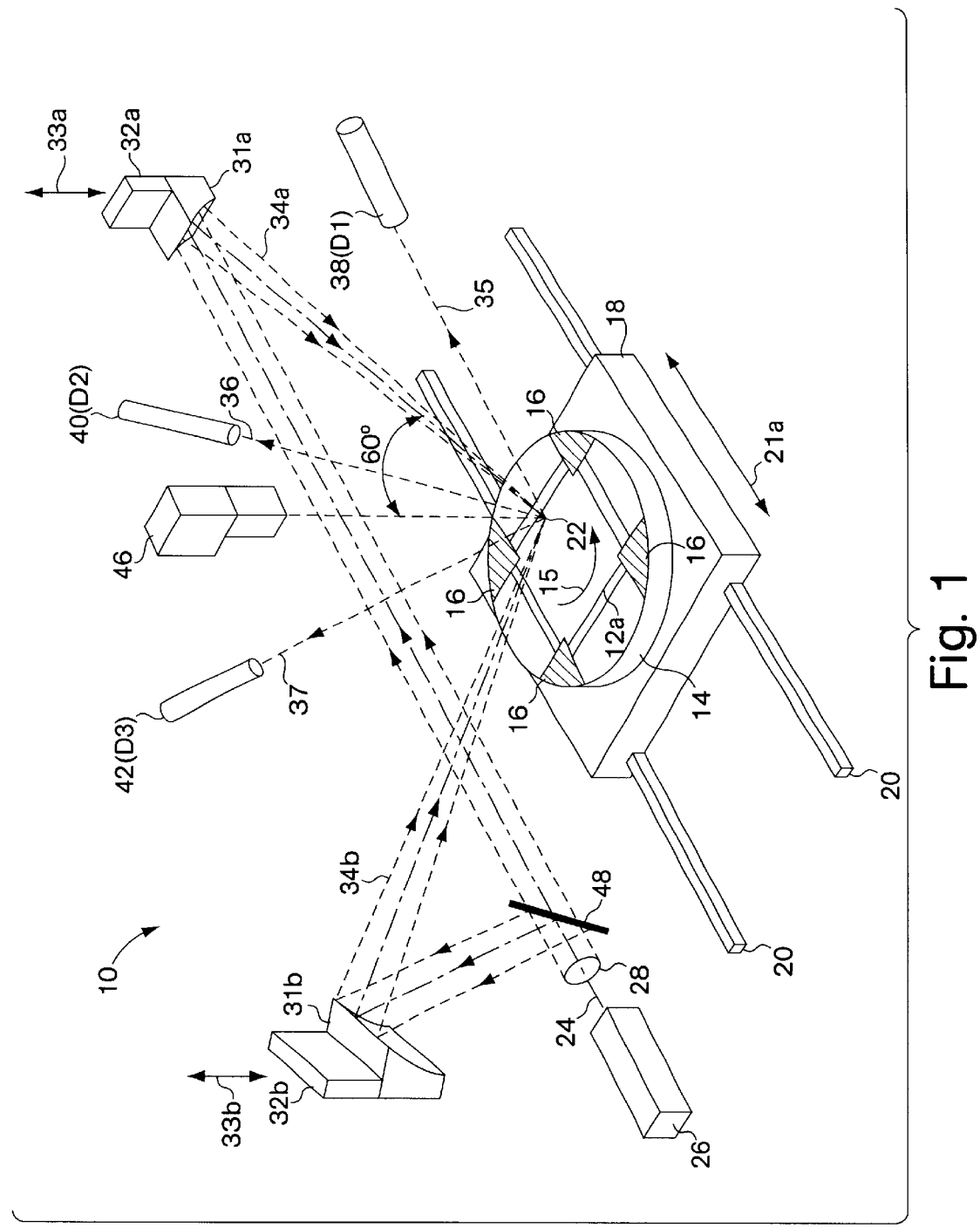
FIG. 1 is a three-dimensional view of an improved optical inspection system in accordance with an embodiment of the present invention.

In one embodiment of the present invention and referring to FIG. 1, an improved high sensitivity optical inspection system 10 is set forth for detecting and distinguishing between flaws and regular patterns defined on a diffractive surface, such as the surface of a plate 12. The plate 12 can be a photo-lithographic mask formed of a glass or quartz substrate which has on one of its surfaces a plurality of chrome patterns. In one embodiment, the plate 12 can have dimensions ranging from approximately 4 to 9 inches in width and 4 to 9 inches in length with a thickness of approximately 0.09 to 0.35 inches.

The plate 12 can be positioned in an object holder 12a. The object holder 12a and plate 12 can be mounted on a rotating plate holder 14 and secured thereon by a releasable attachment mechanism 16, such as reference surfaces or tabs at each corner of the object holder 12a. The plate holder 14 is rotated in the direction of arrow 15 by a spindle (not visible in this figure) and is mounted upon a translation stage 18, which translates in the direction indicated by arrows 21a. The point of inspection 22 is illuminated by either a first laser beam 34a or a second laser beam 34b which are both provided by a stationary ultraviolet laser 26 that generates an ultraviolet laser beam 24. The stationary ultraviolet laser 26 can provide a beam 24 with at least two wavelengths, which in one embodiment are, 351 nm and 364 nm. The laser beam 24 passes through an expander 28 which enlarges the beam 24 into an expanded beam 30. The expanded beam 30 can impinge upon a mirror 48 which redirects the expanded beam 30 upon the reflecting surface of a first off-axis parabolic mirror 31a which provides a first beam 34a and focuses the first beam 34a to a small spot on the surface of the plate 12. The first off-axis parabolic mirror 31a is affixed to a focusing actuator 32a which translates in the direction of arrows 33a. The first off-axis parabolic mirror 31a is positioned to converge the first beam 34a at inspection point 22 at an angle of approximately 60° from an axis defined normal to the surface of plate 12. The mirror 48 can be controlled to pivot for permitting the expanded beam 30 to impinge upon the reflecting surface of a second off-axis parabolic mirror 31b which provides a second beam 34b and focuses the second beam 34b to a small spot on the surface of the plate 12. The second off-axis parabolic mirror 31b is affixed to a second focusing actuator 32b, which translates in the direction of arrows 33b. The second off-axis parabolic mirror 31b is positioned such that it converges the second beam 34b at inspection point 22 at an angle of approximately 60° from the axis defined normal to the surface of plate 12.

During operation of the system 10, the plate holder 14 is rotated and the translation stage 18 translates the plate 12 such that either beam 34a or 34b, at point 22 under inspection, effectively traces a spiral path having a plurality of revolutions on the surface of the plate 12. In an embodiment, the plate holder 14 can be vertically oriented to hold the plate 12 in a vertical position to minimize the amount of contamination of the plate 12 by airborne particles. The first 34a and the second 34b beams can be controlled so that either beam 34a or beam 34b scans the diffractive surface present on the surface of plate 12. Although only two laser beams are used to scan the plate in this configuration, this is not a necessary limitation of the present invention, as a plurality of laser beams can be employed to scan the plate 12.

In an embodiment, the first beam 34a is controlled to scan the diffractive surface present on the surface of the plate 12 when the angle of rotation of the plate 12, with respect to the direction 21a of translation stage 18, is within a first group of predetermined angular sectors. The second beam 34b is controlled to scan the diffractive surface present on the surface of plate 12 when the rotational position of the plate, with respect to the translation stage 18, is within a second group of predetermined angular sectors. The first beam 34a and the second beam 34b are each circumferentially positioned about the plate 12, so that either the first beam 34a or the second beam 34b can impinge upon patterns present on the plate 12 to generate a scattered intensity distribution. Further, the first beam 34a or second beam 34b can be selectively applied to the plate 12 based on the rotational position of the first and second groups of angular sectors defined on the plate 12. For example, the first beam 34a can be applied to the first group of predetermined angular sectors, which are defined on the plate 12, when the first group of predetermined angular sectors comes into close proximity to the first beam. Similarly, the second beam 34a can be applied to the second group of predetermined angular sectors, which are defined on the plate 12, when the second group of predetermined angular sectors comes into close proximity to the second beam. Therefore, based on the circumferential positioning of the first 34a and second 34b beams and the angular position of the first and second groups of predetermined angular sectors, which are defined on the plate 12, either the beam 34a or the beam 34b can be selectively applied to the plate 12. Moreover, either beam 34a or beam 34b can be selectively applied to the plate 12 based on which beam will result in generating a lower detected light pattern scattering. Thus, selectively applying either beam 34a or beam 34b to the plate 12 when either beam will generate a lower detected light pattern scattering can collectively produce a scan pattern on the plate 12, which has an overall reduced sensitivity to light pattern scattering.

In an embodiment, the first beam 34a is circumferentially positioned at approximately 0° with respect to the plate 12 (or at approximately 3 o'clock) and the second beam 34a is circumferentially positioned at approximately 225° (or at approximately between 7 and 8 o'clock) with respect to the plate 12.

In an embodiment, the first group of predetermined angular sectors is defined as ranging from approximately 342.5°–22.5°, 67.5°–112.5°, 157.5°–202.5° and 247.5°–292.5°. The second group of predetermined angular sectors is defined as ranging from approximately 22.5°–67.5°, 112.5°–157.5°, 202.5°–247.5° and 292.5°–342.5°.

A number of light rays 35, 36 and 37 scattered from the point of inspection 22 on the surface of the plate 12 as a result of a flaw or a regular surface pattern is received by the detectors 38, 40 and 42. Light incident upon a regular surface pattern is scattered to produce a number of substantial intensity levels separated by a number of very low intensity levels distributed fairly regularly about the pattern on the surface. Light incident upon a surface flaw, however, produces a fairly uniform high intensity scattering of light about the flaw. Thus, by placing the detectors 38, 40 and 42 in the regions where low levels of scattered light from patterns are expected, the system 10, as described in detail below, can readily distinguish between flaws and surface patterns by determining the minimum detected intensity level from the detectors 38, 40 and 42. If a very low level is detected at least by one of the detectors 38, 40 and/or 42, below a predetermined threshold, no flaw is present, while if levels above the threshold are detected by the detectors 38, 40 and/or 42, a surface flaw is present. Although only three detectors are used in this configuration, this is not a necessary limitation of this invention, as any number of detectors greater than three could be used as long as at least some of them are located proximate the expected low scattering directions of the pattern scattering distribution.

In one particular example, when the point of inspection 22 on the surface of the plate 12 is controlled to rotate along the angular range defined by the first group of predetermined angular sectors, the first beam 34a is controlled to scan the point of inspection 22. At the same time, the detectors 38 and 40 receive the scattering of light from either the pattern or flaw defined on the diffractive surface of the plate 12. Utilizing the first beam 34a to inspect portions of the diffractive surface of the plate 12, while the point of inspection 22 is positioned in any one of the first predetermined angular sectors, decreases the intensity of the diffracted light produced by the pattern and received by detectors 38 and 40. The intensity of the diffracted light received by the detectors 38 and 40 is decreased because the radial angle defined between the first beam 34a and the point of inspection 22 is maintained as close to orthogonal as possible while the point of inspection 22 is moved within any one of the first predetermined angular sectors. In this manner, the sensitivity of the system 10 is increased, because the light scattering intensity diffracted from patterns on the diffractive surface can be more accurately distinguished from flaws.

Similarly, utilizing the second beam 34b to inspect other portions of the diffractive surface of the plate 12, defined by the second predetermined angular sectors, decreases the intensity of the diffracted light received by detectors 40 and 42. The intensity of the diffracted light received by detectors 40 and 42 is decreased because the radial angle defined between the second beam 34b and the point of inspection 22 is maintained as close to orthogonal as possible while the point of inspection is moved within any one of the second predetermined angular sectors.

Data collected from the first beam 34a scanning portions of the diffractive surface and data collected from the second beam 34b scanning other portions of the diffractive surface can be added together to provide an improved sensitivity test result for the entire diffractive surface of the plate.

Also included in the system 10 is an auto-focus sensor head 46 which is used to sense plate 12 position and to position accordingly the first 32a and the second 32b off-axis parabolic focusing actuators so that the respective first 34a and second 34b beams are properly focused at the point of inspection 22.

Figure 2:
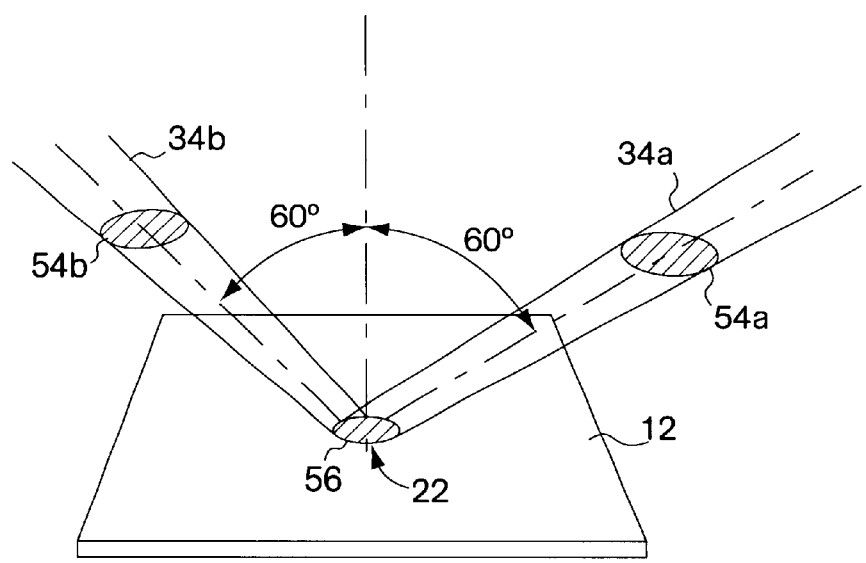
FIG. 2 is an enlarged three-dimensional view of the first and second laser beams projected onto the surface of the plate under inspection shown in the system of FIG. 1.

The first and the second beams 34a and 34b respectively are matched to have the same characteristics and properties. FIG. 2 illustrates characteristics and properties of the first 34a and the second 34b beams. In FIG. 2, the first 34a and the second 34b beams have an elliptical cross-section of approximately 2 by 5 microns as respectively indicated at cross-sections 54a and 54b. When the first 34a and the second 34b beams converge upon the surface of plate 12 an elliptical beam spot 56 is formed at the point of inspection 22. The projected beam spot 56 on the surface of the plate 12 is approximately 2 by 10 microns in size. Conventional inspection systems utilize a beam which produces a spot size between 15 and 50 microns. A large beam spot size results in decreased resolution and sensitivity. Thus, by using an ultraviolet laser for both first 34a and second 34b beams, which produces a smaller beam spot, such as spot 56, the sensitivity and resolution of the system 10 are significantly increased. Further, by using an ultraviolet laser having a shorter wavelength the sensitivity is additionally increased.

Figure 3:
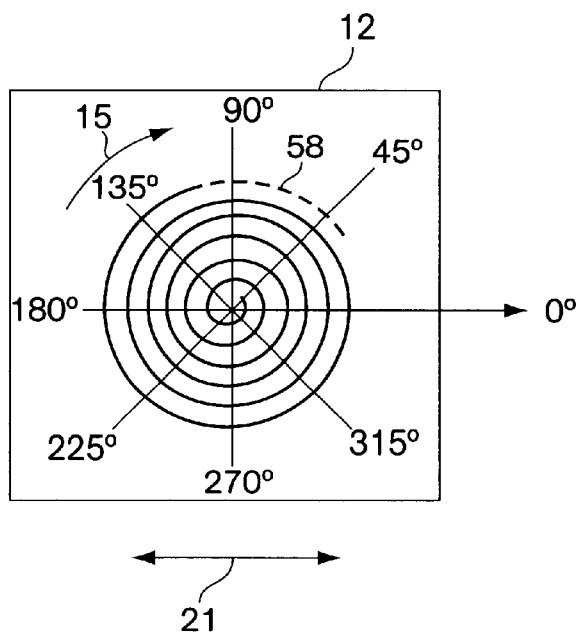
FIG. 3 is a schematic top plan view of a plate under inspection depicting the spiral path of the laser beam traced on the plate surface in the system of FIG. 1.
Figure 4:
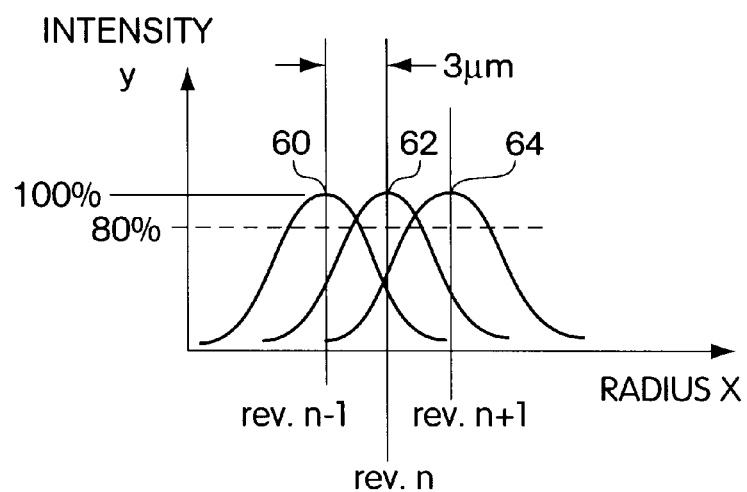
FIG. 4 is a plot of the intensity distribution vs. radius for three adjacent successive traces of the ultraviolet laser beam on the plate.

In order to inspect the entire surface of the plate 12 with the first 34a and the second 34b beams, the plate 12 is rotated in the direction of arrow 15 (FIG. 1) and translated in the direction of arrows 21a (FIG. 1) such that a spiral path 58, as shown in FIG. 3, of the first 34a and the second 34b beams are traced on the surface of the plate 12. In order to insure adequate overlap of adjacent revolutions of the spiral path 58, the trace pitch (distance from the center of each beam revolution to the center of its adjacent revolutions) of the spiral is set at approximately 3 microns. This is illustrated in FIG. 4 where the intensity profiles of three successive revolutions (N−1, N, N+1) of the spiral trace 58 are shown as revolutions 60, 62 and 64, respectively. Revolutions 60, 62 and 64 represent a plot of the intensity of the trace, which is indicated on the Y axis versus the radius which is indicated on the X axis. By selecting a 3 micrometer pitch (the centers of successive revolutions are spaced 3 micrometers apart) with a 2 by 10 micrometer beam, adequate overlap is obtained as shown at the 80% intensity level of both the first 34a and the second 34b beams. It is known from the Gaussian profile of the first 34a and the second 34b beams that at 80% intensity the first 34a and second 34b beam widths will be approximately 3.33 microns. Thus, by choosing a 3 micron pitch adequate overlap is insured and no portion of surface 12 between successive revolutions of spiral trace 58 is left un-inspected.

Figure 6A:
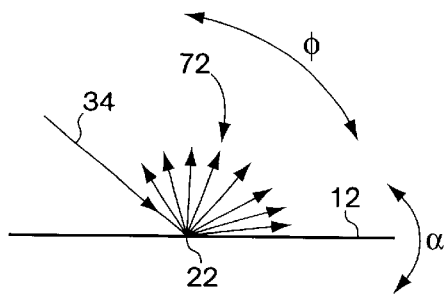
FIG. 6A is a schematic view of the scattered intensity distribution as a result of an ultraviolet laser beam impinging upon a particle.
Figure 6B:
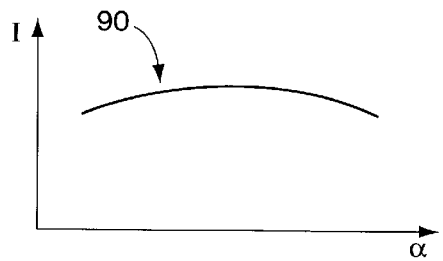
FIG. 6B is a plot of the intensity of the scattering distribution of FIG. 6A over the range of angles about the point under inspection.
Figure 7:
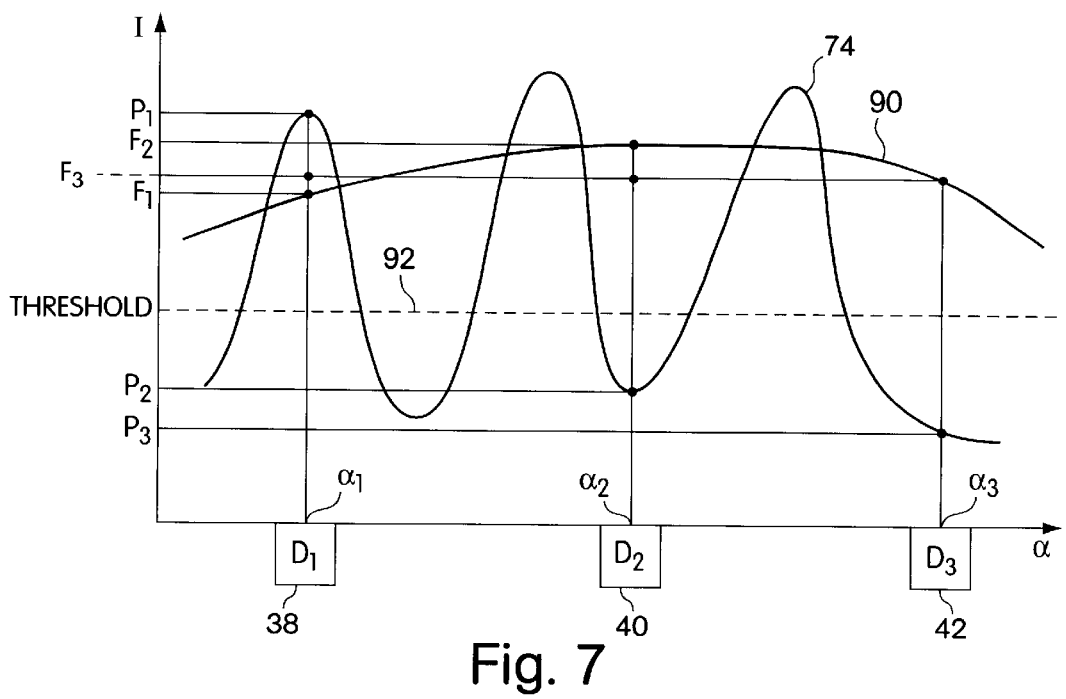
FIG. 7 is a plot which includes the angular intensity distributions depicted in FIGS. 5B and 6B superimposed.

The scattered light intensity distributions of FIGS. 5–7 illustrate that light scattered from regular surface patterns produce intensity distributions which have peaks of substantial magnitude, well defined, and separated by regions which are at or below the noise level. In contrast, light scattered from flaws produce a substantially uniform high intensity level with no low intervals.

Figure 5A:
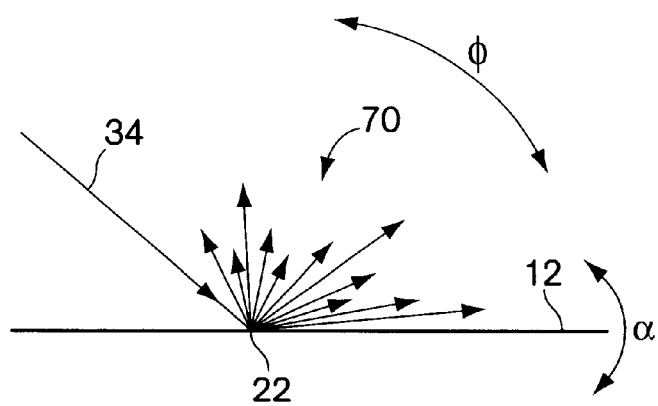
FIG. 5A is a schematic view of the scattered intensity distribution as a result of an ultraviolet laser beam impinging upon a surface pattern.

FIG. 5A shows a scattered light distribution 70 which results from the first 34a or the second 34b laser beams impinging upon a regular surface pattern at the point of inspection 22. The distribution of surface light scattering is not uniform over the ranges of angles φ with respect to the illuminating beams 34a or 34b. Rather, the distribution of surface light scattering has a number of varying intensity levels, some are at fairly high intensities while others are at much lower intensities. In contrast, as shown in FIG. 6A, scattered light distribution 72 which results from the first 34a or the second 34b beams impinging upon a flaw at the point of inspection 22 on the surface of plate 12 which produces a more uniform scattered light distribution over the range of angles φ. The scattered light from a flaw and a surface pattern over angles φ are distributed similarly over the range of angles α azimuthally about point of inspection 22. Thus, scattered light distributions 70 and 72 are actually three-dimensional semi-spherical scattered light distributions. Distribution 72 is approximately a uniform semi-spherical distribution while distribution 70 is a distribution with a number of peaks and low levels.

Figure 5B:
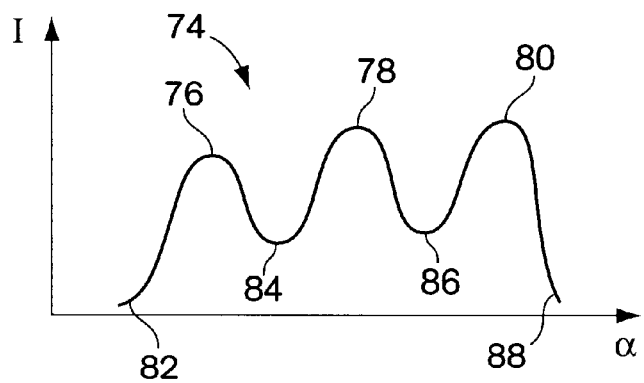
FIG. 5B is a plot of the intensity of the scattered intensity distribution of FIG. 5A over the range of angles about the point under inspection.

The intensity levels of the light distributions scattered from both the regular surface pattern and flaw over a range of angles α about point of inspection 22 are shown in FIGS. 5B and 6B, respectively. In FIG. 5B the intensity response 74 of scattered light distribution 70 from a pattern is shown to include a number of peaks 76, 78 and 80 as well as a number of lower levels 82, 84, 86 and 88 over the range of angles α. In contrast, intensity response 90 of scattered light distribution 72 from a flaw about the range of angles α about point of inspection 22 is much more uniform. The intensity level is nearly equal over the range of angles in which light is detected.

The pattern intensity response 74 and the flaw intensity response 90 are superimposed and the intensity levels detected by the detectors 38 (D1), 40 (D2) and 42(D3), are shown in FIG. 7. FIG. 7 demonstrates how the high sensitivity optical inspection system 10 of the present invention differentiates between flaws and surface patterns. The detector 38 (D1) located at angle α1 receives a light intensity level F1 when scattered light distribution 72 is generated because of the presence of a flaw on the surface of plate 12. Detector 40 (D2) at angle α2 detects a light intensity F2. Detector 42 (D3) at angle α3 detects a light intensity F3. The system according to this invention, as described below, determines the minimum detected intensity level, which in this case is F1, and compares that level to threshold level 92. If the minimum detected intensity level from the detectors 38 (D1), 40 (D2) and 42 (D3) exceed threshold level 92, a flaw is present at the point of inspection. From the level of intensity detected the approximate particle size can be determined: the greater the intensity the greater the flaw size. If, on the other hand, a regular surface pattern causes scattered light distribution 70, detector 38 (Dl) at angle α1 detects intensity level P1, while detector 40 (D2) at angle α2 detects level P2 and detector 42 (D3) at angle α3 detects level P3. Intensity level P3 is then determined to be the minimum detected intensity level and since this level is below threshold 92 the system indicates that a regular surface pattern has been detected at the point of inspection and that no flaw is present.

Regular surface patterns produce very similar scattered light distributions which have low intensity levels such as levels 82, 84, 86, 88, as shown in FIG. 5B, which regularly are present in known locations about the point of inspection on a surface. Thus, it is desirable to locate detectors 38, 40 and 42 (and any additional detectors) at locations about the surface under inspection where low scattered light intensity levels from patterns are expected. The Threshold level 92 is variable, however, it must always be set slightly higher than the minimum level expected to be detected from one of the detectors as a result of a surface pattern. Thus, this level limits the minimum size flaw that can be detected. Flaws which have an intensity response 90 which is less than the lowest possible threshold 92 or lower than the lowest detected intensity level of pattern response 74 will not be detected as a flaw. The lower limit on this system 10 is approximately an average of 0.2 micron flaw detection.

Figure 8:
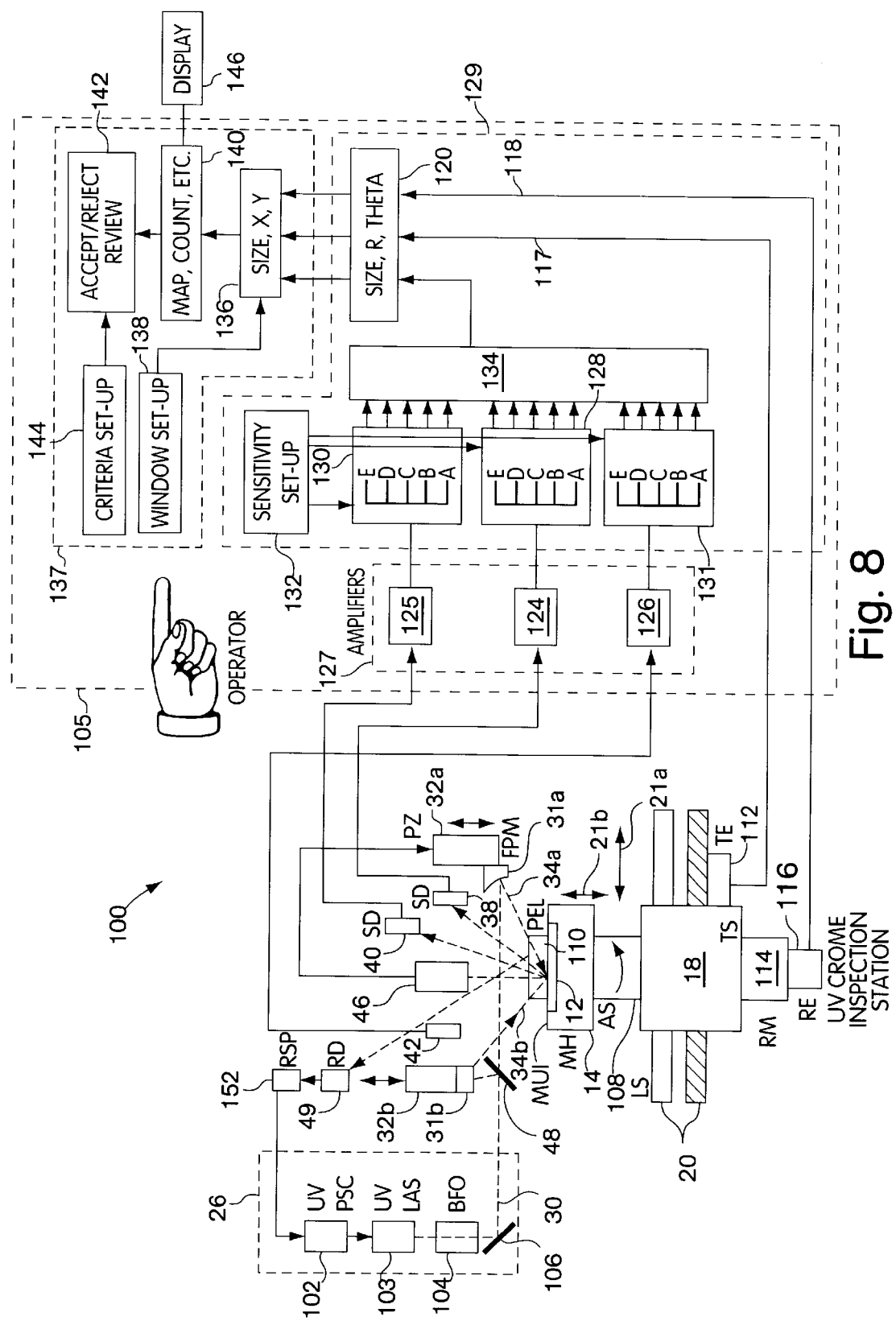
FIG. 8 is a schematic block diagram of an optical inspection station in accordance with the present invention.

Referring to FIG. 8, an optical inspection station 100 is set forth which includes the optical inspection system 10 previously described with respect to FIG. 1., as well as a detection circuit 105. The detection circuit 105 includes an analog signal processing circuit 127 coupled to the detectors 38, 40, and 42. The detection circuit further includes a digital signal processing circuit 129 which is coupled to the analog signal processing circuit and a computer control and data storage unit 137 which is coupled to the digital signal processing circuit 137.

The analog signal processing circuit 127 includes a plurality of amplifiers 124, 125 and 26. Each amplifier 124, 125 or 126 can be coupled to at least one of the detectors 38, 40, or 42. Further, each amplifier 124, 125 or 126 can be coupled to a sensitivity circuit 132 to enable the sensitivity of each amplifier 124, 125 or 126 to be adjusted.

The digital signal processing circuit includes a plurality of signal comparators 128, 130, and 131, each comparator 128, 130, or 131 can be coupled to at least one of the amplifiers 124, 125 or 126. The digital signal processing circuit 129 further includes a minimizer circuit 134 which can be coupled to the signal comparators 128, 130, and 131. The minimizer circuit 134 can be further coupled to a polar coordinate particle detector 120.

The computer control and data storage unit 137 includes a Cartesian conversion program 136 which is in communication with the polar coordinate particle detector 120 defined in the digital signal processing circuit 129. The Cartesian conversion program 136 is in further communication with a flaw mapping program 140. The flaw mapping program 140 can be in further communication with an accept and/or reject program 142.

The optical inspection station 100 further includes a laser source 26 having ultraviolet laser power supply and control 102 which drives ultraviolet laser 103. Ultraviolet laser 103 through beam forming optics 104 produces a laser beam 30 which is provided to mirrors 106 and 48 to redirect laser beam 30 to either the first off-axis parabolic mirror 31a or to the second off-axis parabolic mirror 31b. The first 31a or the second 31b off-axis parabolic mirror can respectively form the first 34a or the second 34b converging beam which can be focussed onto the surface of plate 12. Plate 12 is mounted within plate holder 104 which itself is mounted upon and rotated in the counter clockwise direction by rotation spindle 108. There is included a pellicle 110 which protects plate 12.

Pellicle 110, plate 12, plate holder 14 and rotation spindle 108 are all mounted on translation stage 18 which translates upon rails 20 in the direction of arrows 21a. Rotation spindle can also be moved in the direction of arrow 21b to adjust the height of plate 12. Translation encoder 112 tracks the precise radial position of point under inspection 22 on plate 12 from the starting point of the inspection. Rotation motor 114 drives rotation spindle 108, and rotation encoder 116 tracks the precise rotational (angular) position of plate 12 and hence the loction of point under inspection 22 on the surface of plate 12. The translational and rotational signals are provided over lines 117 and 118, respectively, to polar coordinate particle detector 120. Also input to polar coordinate flaw detector 120 is a signal indicative of the size of the flaw detected or a zero level signal if a pattern or nothing is detected on the surface of plate 12. Thus, flaw detector 120 provides an output of the polar coordinates of a located flaw on surface 12 and the flaw size.

The location and size of a detected flaw is determined first by detecting the level of the scattered light distribution received by detectors 38, 40 and 42 from the ultraviolet illumination of a point of inspection 22 on the surface of plate 12. Detectors 38, 40 and 42 provide an electrical signal corresponding to the intensity of light detected over lines 121, 122 and 123 to amplifiers 124, 125 and 126, respectively, within analog signal processing circuit 127. The amplified signals are provided to signal comparators 128, 130 and 131 within digital signal processing circuit 129. Comparators 128, 130 and 131, which may be LT1016 circuits produced by Linear Technology, each output a digital word to minimizer 134. A comparator output signal equal to zero indicates that neither detector 38, 40 nor 42 detected an intensity level which is above the threshold level. Signals that exceed the threshold level produce different digital words that correspond to the size of the signal and hence the size of the flaw detected. In this example only five different flaw sizes (A–E) are shown, however, a greater number of sizes could be used. Sensitivity set-up circuit 132 enables the adjustment of the levels A–E so that an operator can vary the sensitivity level for different applications. The digital words corresponding to the signals detected from comparators 128, 130 and 131 are provided to minimizer 134 which outputs the minimum intensity level detected by detectors 38, 40 and 42. If the digital output from minimizer 134 is equal to zero this indicates that no flaw detection occurred on plate 12. A non-zero output indicates that a flaw is present and the data is provided to polar coordinate particle detector 120 which simultaneously receives the polar coordinates, R and θ, of the location of the flaw detected from translational and rotational encoders 112 and 116, respectively. The flaw size and the polar coordinates are provided to Cartesian conversion program 136 within computer control and data storage unit 137, which converts the polar coordinates R and θ to Cartesian coordinates X and Y and receives the flaw size signal. A window set-up program 138 enables the operator to input the size of the plate 12 and its quality area under inspection so that the proper Cartesian coordinates X and Y can be determined, e.g. only the area within the pellicle frame.

Figure 9:
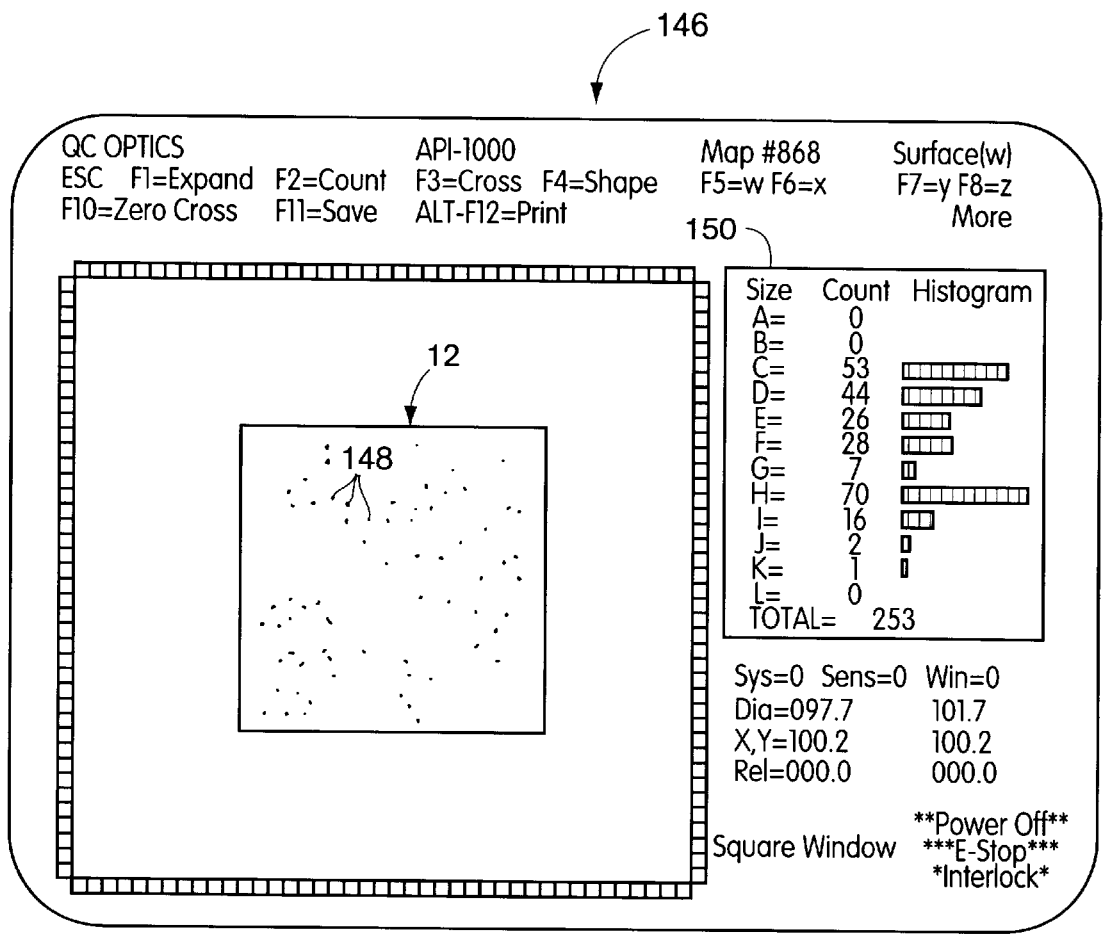
FIG. 9 is a detailed view of an image showing locations of the detected flaws produced on the display shown in FIG. 8.

The Cartesian coordinates and flaw size are provided to flaw mapping program 140 which stores the location and size of each flaw detected. After the entire surface of plate 12 has been inspected and the location and size of each flaw on the surface of plate 12 has been stored by flaw mapping program 140, accept/reject program 142 makes a determination based on certain criteria provided by an operator-defined parameter list 144 whether or not to accept or reject the particular plate under inspection. For example, if the total number of flaws detected exceeds a predetermined number or if a predetermined number of certain size flaws is exceeded then the plate is rejected. Flaw mapping program 140 also provides the location and flaw size information to display 146. A detailed view of the display 146 is shown in FIG. 9. The display 146 provides the user with a depiction of the flaw locations on plate 12. A map of plate 12 having a number of flaws 148 is displayed. Also, the total flaw count on plate 12 as well as the count of each different flaw size is shown in display portion 150.

Also included in station 100 is reflectometer detector 49 which detects the specularly reflected light from the surface of pellicle 110 and provides a signal to reflectometer signal processing 152 which in turn provides a control signal to ultraviolet laser power supply and control 102. The signal from reflectometer signal processing 152 increases the ultraviolet laser power and control signal to ultraviolet laser 103 in order to increase the intensity of laser beam 30 output from laser source 26 to compensate for the light reflected from the surface of pellicle 110 which attenuates the input beam and the scattered light signal received by detectors 38, 40 and 42. Or, sensitivity levels in detectors 38, 40 and 42 are accordingly increased.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting.

What is claimed is:

1. An optical inspection system that detects flaws on a diffractive surface containing surface patterns, comprising:
    at least one optical source that provides a first beam, the first beam illuminating a first region of the diffractive surface and generating a first scattered intensity distribution, the optical source providing a second beam, the second beam illuminating a second region of the diffractive surface distinct from the first region and generating a second scattered intensity distribution;
    a plurality of detectors positioned about the diffractive surface, the detectors detecting the first and second scattered intensity distributions; a detection circuit coupled to the detectors that determines if a flaw is present on the diffractive surface; and a movable mounting table that securely retains the diffractive surface, the mounting table moving the diffractive surface with respect to the first and second beams to generate a scan pattern on the diffractive surface.

2. The optical inspection system of claim 1, wherein the optical source includes an optical light emitter and a first mirror that receives and redirects an optical beam provided by the optical light emitter to provide the first beam.

3. The optical inspection system of claim 2, wherein the optical source further includes a second mirror that receives and redirects the optical beam provided by the optical light emitter to provide the second beam.

4. The optical inspection system of claim 3, wherein the first and second mirrors each include an off-axis parabolic mirror.

5. The optical inspection system of claim 3, wherein the optical source further includes a pivotable mirror that receives the optical beam, the pivotable mirror being pivoted to a first position to redirect the optical beam to the first mirror and the pivotable mirror being pivoted to a second position to redirect the optical beam to the second mirror.

6. The optical inspection system of claim 1, wherein the detection circuit includes circuitry to determine a minimum detected intensity level.

7. The optical inspection system of claim 6, wherein the detection circuit further includes circuitry to process the minimum detected intensity level to determine if a flaw is present on the diffractive surface.

8. The optical inspection system of claim 7, wherein the detection circuit further includes circuitry to determine flaw size.

9. The optical inspection system of claim 8, wherein the mounting table includes an encoder that determines the position of the illuminated region on the diffractive surface.

10. The optical inspection system of claim 9, wherein the detection circuit further includes circuitry to determine the location of flaws on the diffractive surface based on the position of the illuminated region on the diffractive surface and circuitry to store the location of the flaws.

11. The optical inspection system of claim 10, wherein the system further includes a display that displays the flaws and their locations.

12. The optical inspection system of claim 1, wherein the detection circuit includes:
   an analog signal processing circuit coupled to the detectors;
   a digital signal processing circuit coupled to the analog signal processing circuit; and
   a computer control and data storage unit coupled to the digital signal processing circuit.

13. The optical inspection system of claim 12, wherein the analog signal processing circuit includes a plurality of amplifiers, each amplifier being coupled to at least one detector.

14. The optical inspection system of claim 13, wherein each amplifier is coupled with a sensitivity circuit to enable the sensitivity of each amplifier to be adjusted.

15. The optical inspection system of claim 13, wherein the digital signal processing circuit includes a plurality of signal comparators, each comparator being coupled to at least one amplifier.

16. The optical inspection system of claim 15, wherein the digital signal processing circuit further includes a minimizer circuit coupled to the signal comparators, the minimizer circuit being further coupled to a polar coordinate particle detector.

17. The optical inspection system of claim 16, wherein the computer control and data storage unit includes a cartesian conversion program which is in communication with the polar coordinate particle detector, the cartesian conversion program being in further communication with a flaw mapping program, the flaw mapping program being in communication with an accept and/or reject program.

18. The optical inspection system of claim 1, wherein the mounting table includes a rotatably mounted plate holder and a slideable translation stage, the mounting table rotating and translating the diffractive surface to establish the scan pattern, the scan pattern including a spiral trace having a plurality of revolutions of the first and second beams on the diffractive surface.

19. The optical inspection system of claim 1, wherein the first beam is controlled to illuminate the first region defined on the diffractive surface which includes a first group of angular sectors including: 342.5°–22.5°, 67.5°–112.5°, 157.5°–202.5° and 247.5°–292.5°.

20. The optical inspection system of claim 1, wherein the second beam is controlled to illuminate the second region defined on the diffractive surface which includes a second group of angular sectors including: 22.5°–67.5°, 112.5°–157.5°, 202.5°–247.5° and 292.5°–342.5°.

21. The optical inspection system of claim 1, wherein the optical light emitter includes an ultra violet laser.

22. The optical inspection system of claim 21, wherein the ultraviolet laser projects an elliptical beam spot on the diffractive surface.

23. The optical inspection system of claim 22, wherein the ultraviolet laser beam impinges on the diffractive surface at an angle of approximately 60° from normal to the surface.

24. The optical inspection system of claim 23, wherein the beam width is at least as large as the beam trace pitch to ensure inspection of the regions between revolutions of the trace.

25. The optical inspection system of claim 24, wherein the beam trace pitch is no greater than approximately 3 micrometers.

26. The optical inspection system of claim 1, wherein the plurality of detectors includes:
   a first detector positioned at a first location proximate the diffractive surface to detect the intensity level of the scattered intensity distribution at the first location;
   a second detector positioned at a second location proximate the diffractive surface to detect the intensity level of the scattered intensity distribution at the second location; and
   a third detector positioned at a third location proximate the diffractive surface to detect the intensity level of the scattered intensity distribution at the third location.

27. A method of using an optical inspection system to inspect a diffractive surface containing surface patterns to detect flaws on the diffractive surface, the method comprising the steps of:
   (i) illuminating a first region of the diffractive surface with a first beam to generate a first scattered intensity distribution;
   (ii) illuminating a second region of the diffractive surface distinct from the first region with a second beam to generate a second scattered intensity distribution;
   (iii) detecting an intensity level of the first and second scattered intensity distributions generated by the first and second beams, the intensity level being detected at a plurality of locations about the diffractive surface;
   (iv) processing the detected intensity level of the first and second scattered intensity distributions to determine if a flaw is present; and (v) moving the diffractive surface to generate a scan pattern on the diffractive surface, the scan pattern covering the entire diffractive surface.

28. The method of using the optical inspection system of claim 27, wherein the step of processing the detected intensity level further includes indicating the absence of a flaw on the illuminated region of the diffractive surface when the detected intensity level is below a predetermined threshold level and indicating the presence of a flaw on the illuminated region of the diffractive surface when the detected intensity level exceeds the predetermined threshold intensity level.

29. The method of using the optical inspection system of claim 27, wherein the step of illuminating the first region of the diffractive surface with the first beam includes illuminating a first group of predetermined angular sectors defined on the diffractive surface.

30. The method of using the optical inspection system of claim 27, wherein the step of illuminating the second region of the diffractive surface with the second beam includes illuminating a second group of predetermined angular sectors defined on the diffractive surface.

31. The method of using the optical inspection system of claim 29, wherein the step of illuminating the first group of predetermined angular sectors defined on the diffractive surface with the first beam includes projecting an elliptical beam spot onto the diffractive surface.

32. The method of using the optical inspection system of claim 31, wherein the step of illuminating the first group of predetermined angular sectors defined on the diffractive surface with the first beam further includes directing an ultraviolet laser beam to the diffractive surface at an angle of approximately 60° from normal to the diffractive surface.

33. The method of using the optical inspection system of claim 30, wherein the step of illuminating the second group of predetermined angular sectors defined on the diffractive surface with the second optical beam includes projecting an elliptical beam spot onto the diffractive surface.

34. The method of using the optical inspection system of claim 33, wherein the step of illuminating the second group of predetermined angular sectors defined on the diffractive surface with the second beam further includes directing an ultraviolet laser beam to the diffractive surface at an angle of approximately 60° from normal to the diffractive surface.

35. The method of using the optical inspection system of claim 27, wherein the step of moving the diffractive surface to generate the scan pattern on the diffractive surface includes rotating and translating the diffractive surface to establish a spiral trace with a plurality of revolutions of the first and second beams on the diffractive surface.

36. The method of using the optical inspection system of claim 35, wherein the step of rotating and translating includes overlapping each said revolution of said spiral trace with adjacent revolutions to insure inspection of the regions between each revolution.

37. The method of using the optical inspection system of claim 36, wherein the step of rotating and translating includes spacing said revolutions no greater than approximately 3 micrometers apart.

38. The method of using the optical inspection system of claim 27, wherein the step of detecting includes:
detecting the intensity level of the first and second scattered intensity distribution at a first location proximate the diffractive surface;
detecting the intensity level of the first and second scattered intensity distribution at a second location proximate the diffractive surface; and
detecting the intensity level of the first and second scattered intensity distribution at a third location proximate the diffractive surface.

39. The method of using the optical inspection system of claim 38, wherein the step of detecting further includes detecting the intensity level of the first and second scattered intensity distributions at locations about the diffractive surface where the intensity level of the first and second scattered intensity distributions from the surface pattern is expected to be below the threshold intensity level.

40. The method of using the optical inspection system of claim 27, further includes the step of determining flaw size.

41. The method of using the optical inspection system of claim 27, wherein the step of moving the diffractive surface to generate the scan pattern includes determining the position of the illuminated region on the diffractive surface.

42. The method of using the optical inspection system of claim 41, further including the step of determining the location of flaws on the diffractive surface based on the position of the illuminated region on the diffractive surface.

43. The method of using the optical inspection system of claim 42, further including the step of storing the locations and sizes of the flaws.

44. The method of using the optical inspection system of claim 43, further including the step of displaying the flaws and locations on a display.

45. An optical inspection system that detects flaws on a diffractive surface containing surface patterns, the optical inspection system comprising:
means for illuminating a first region of the diffractive surface to generate a first scattered intensity distribution;
means for illuminating a second region of the diffractive surface distinct from the first region to generate a second scattered intensity distribution;
means for detecting the first scattered intensity distribution and the second scattered intensity distribution and determining if a flaw is present on the diffractive circuit.

46. The optical inspection system of claim 45, wherein the means for illuminating the first region of the diffractive surface includes a means for generating a first optical beam.

47. The optical inspection system of claim 46, wherein the means for illuminating the first region of the diffractive surface further includes a means for directing the first optical beam to the first region of the diffractive surface.

48. The optical inspection system of claim 45, wherein the means for illuminating the second region of the diffractive surface includes a means for generating a second optical beam.

49. The optical inspection system of claim 48, wherein the means for illuminating the second region of the diffractive surface further includes a means for directing the second optical beam to the second region of the diffractive surface.

50. The optical inspection system of claim 45, wherein the means for detecting includes a means for determining a minimum detected intensity level.

51. The optical inspection system of claim 50, wherein the means for detecting further includes a means for processing the minimum detected intensity level to determine if a flaw is present on the diffractive surface.

52. The optical inspection system of claim 51, wherein the means for detecting further includes a means for determining flaw size.

53. The optical inspection system of claim 52, wherein the means for detecting further includes a means for determining a location of the flaws on the diffractive surface and a means for storing the location of the flaws.

54. The optical inspection system of claim 45, wherein the system further includes a means for rotating and translating the diffractive surface to generate a scan pattern on the diffractive surface.

* * * * *